United States Patent
Lin

(10) Patent No.: US 11,751,758 B2
(45) Date of Patent: Sep. 12, 2023

(54) INTRAORAL SCANNER WITH FAN GENERATING AIRFLOW THROUGH HEAT-DISSIPATING STRUCTURE

(71) Applicant: QISDA CORPORATION, Taoyuan (TW)

(72) Inventor: Chih-Ying Lin, Taoyuan (TW)

(73) Assignee: Qisda Corporation, Taoyuan (TW)

( * ) Notice: Subject to any disclaimer, the term of this patent is extended or adjusted under 35 U.S.C. 154(b) by 415 days.

(21) Appl. No.: 16/904,576

(22) Filed: Jun. 18, 2020

(65) Prior Publication Data

US 2020/0405140 A1 Dec. 31, 2020

(30) Foreign Application Priority Data

Jun. 28, 2019 (CN) .......................... 201910571377.5

(51) Int. Cl.
*A61B 1/12* (2006.01)
*A61B 5/00* (2006.01)

(52) U.S. Cl.
CPC .............. *A61B 1/12* (2013.01); *A61B 5/0062* (2013.01); *A61B 5/0088* (2013.01); *A61B 2560/02* (2013.01); *A61B 2560/04* (2013.01)

(58) Field of Classification Search
CPC ....... A61B 1/12; A61B 5/0062; A61B 5/0088; A61B 2560/02; A61B 2560/04; A61B 1/0684; A61B 1/00124; A61B 1/00172; A61B 1/00194; A61B 1/247; A61B 1/128; A61C 19/04; H05K 7/20136
USPC .......................................................... 348/66
See application file for complete search history.

(56) References Cited

U.S. PATENT DOCUMENTS

| | | | |
|---|---|---|---|
| 2014/0235156 A1* | 8/2014 | Li | H05K 7/20154 454/184 |
| 2020/0144764 A1* | 5/2020 | Hanselmann | H01R 4/02 |
| 2020/0245849 A1* | 8/2020 | Suzuki | A61B 1/00124 |
| 2020/0288951 A1* | 9/2020 | Zilligen | A61B 1/00068 |
| 2022/0233138 A1* | 7/2022 | Havasi | A61B 5/4547 |

FOREIGN PATENT DOCUMENTS

| | | | | |
|---|---|---|---|---|
| CN | 104010471 A | | 8/2014 | |
| CN | 106073688 | * | 11/2016 | ............ A61B 1/005 |
| JP | 3164281 U | * | 11/2010 | |
| JP | 2013034546 A | * | 2/2013 | |
| KR | 10-2017-0142383 A | | 12/2017 | |

* cited by examiner

*Primary Examiner* — Marnie A Matt

(57) ABSTRACT

An intraoral scanner includes a device body and a connection portion. The device body has a heat-dissipating structure and a first electrical connection port. The connection portion is detachably connected to the device body and includes a second electrical connection port and a fan. The second electrical connection port is electrically connected to the first electrical connection port. The fan generates an airflow that flows through the heat-dissipating structure.

10 Claims, 8 Drawing Sheets

INTRAORAL SCANNER WITH FAN GENERATING AIRFLOW THROUGH HEAT-DISSIPATING STRUCTURE

BACKGROUND OF THE INVENTION

1. Field of the Invention

The present invention relates to an intraoral scanner, and more particularly to a handheld intraoral scanner.

2. Description of the Prior Art

Intraoral scanners are used for 3D scanning of tooth shape. Handheld intraoral scanners are small in size and high in power consumption, which heats the device casing and causes the surface thereof to become hot. Hence, a fan inside the device casing is required for dissipating heat in principle, so that the temperature of the surface can be reduced to be lower than that required by safety regulations. For the fan, the device casing needs to have a hole structure for the fan to guide the airflow to dissipate heat. However, the hole structure will make it easy to accumulate dirt inside the device casing, which makes the device unable to be waterproof in principle, so that the device is not suitable for direct flushing or soaking for sterilization, which makes cleaning the device very difficult.

SUMMARY OF THE INVENTION

An objective of the invention is to provide an intraoral scanner, which adopts a combined design which can take into account the needs of cleaning its body and heat dissipation.

An intraoral scanner according to the invention includes a device body and a connection portion. The device body has a heat-dissipating structure and a first electrical connection port. The connection portion is detachably connected to the device body and includes a second electrical connection port and a fan. The second electrical connection port and the first electrical connection port are connected. The fan generates an airflow that flows through the heat-dissipating structure.

Compared with the prior art, in the intraoral scanner according to the invention, the connection portion together with the fan can be detached from the device body, so that the device body can be cleaned and sterilized individually without being affected by the fan and other related structures. Therefore, the invention can effectively solve the problem in the prior art that the intraoral scanners are difficult to be cleaned and sterilized.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
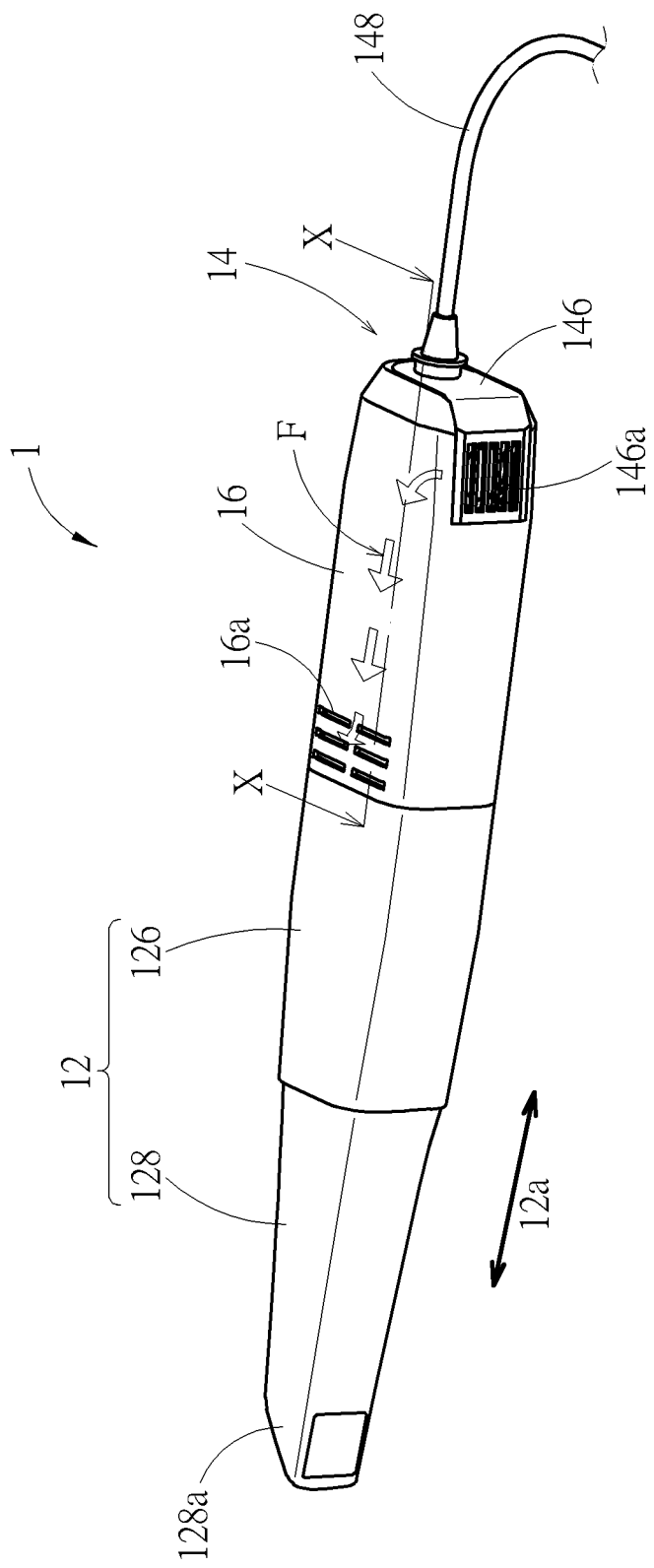
FIG. 1 is a schematic diagram illustrating an intraoral scanner according to an embodiment.
Figure 2:
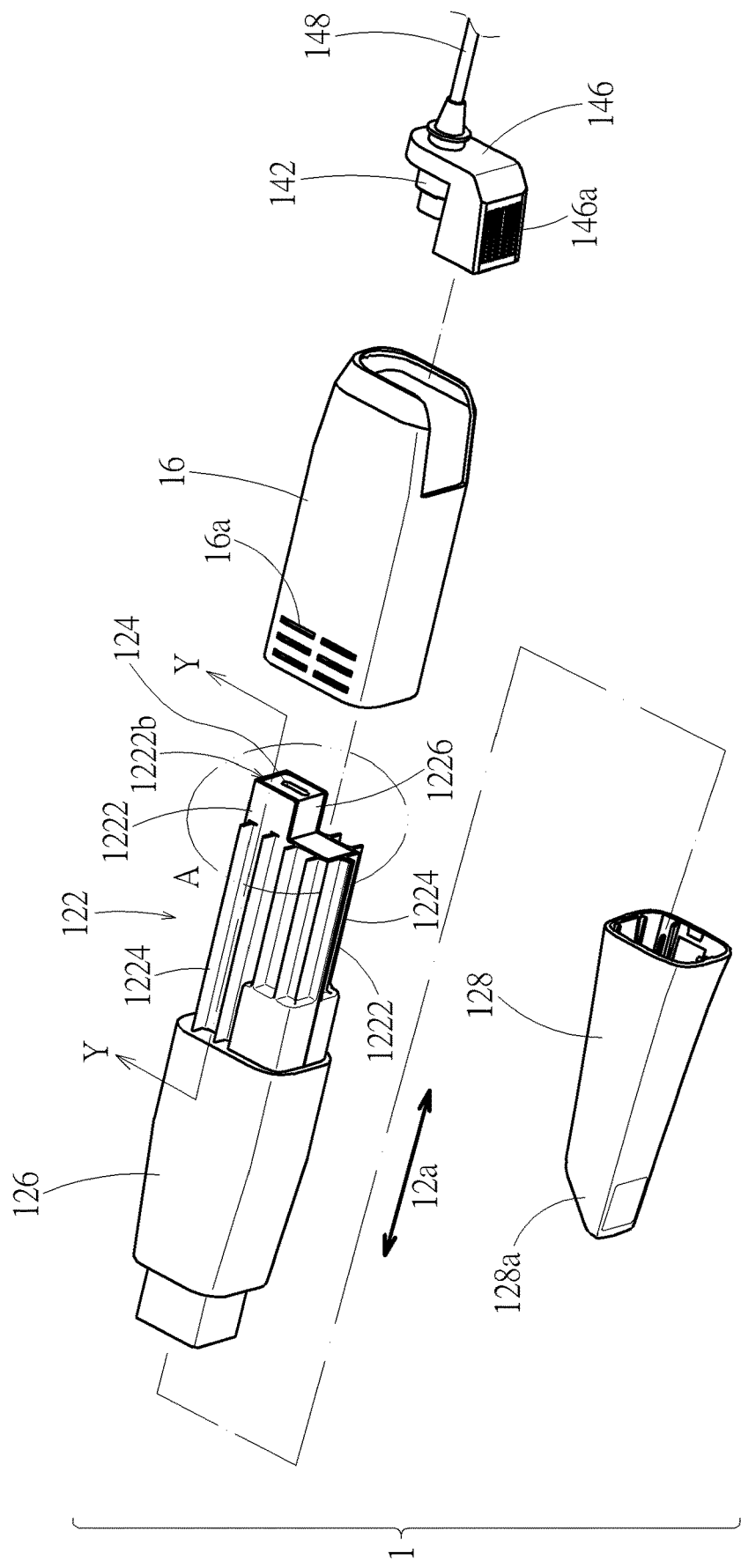
FIG. 2 is a partially exploded view of the intraoral scanner in FIG. 1.
Figure 3:
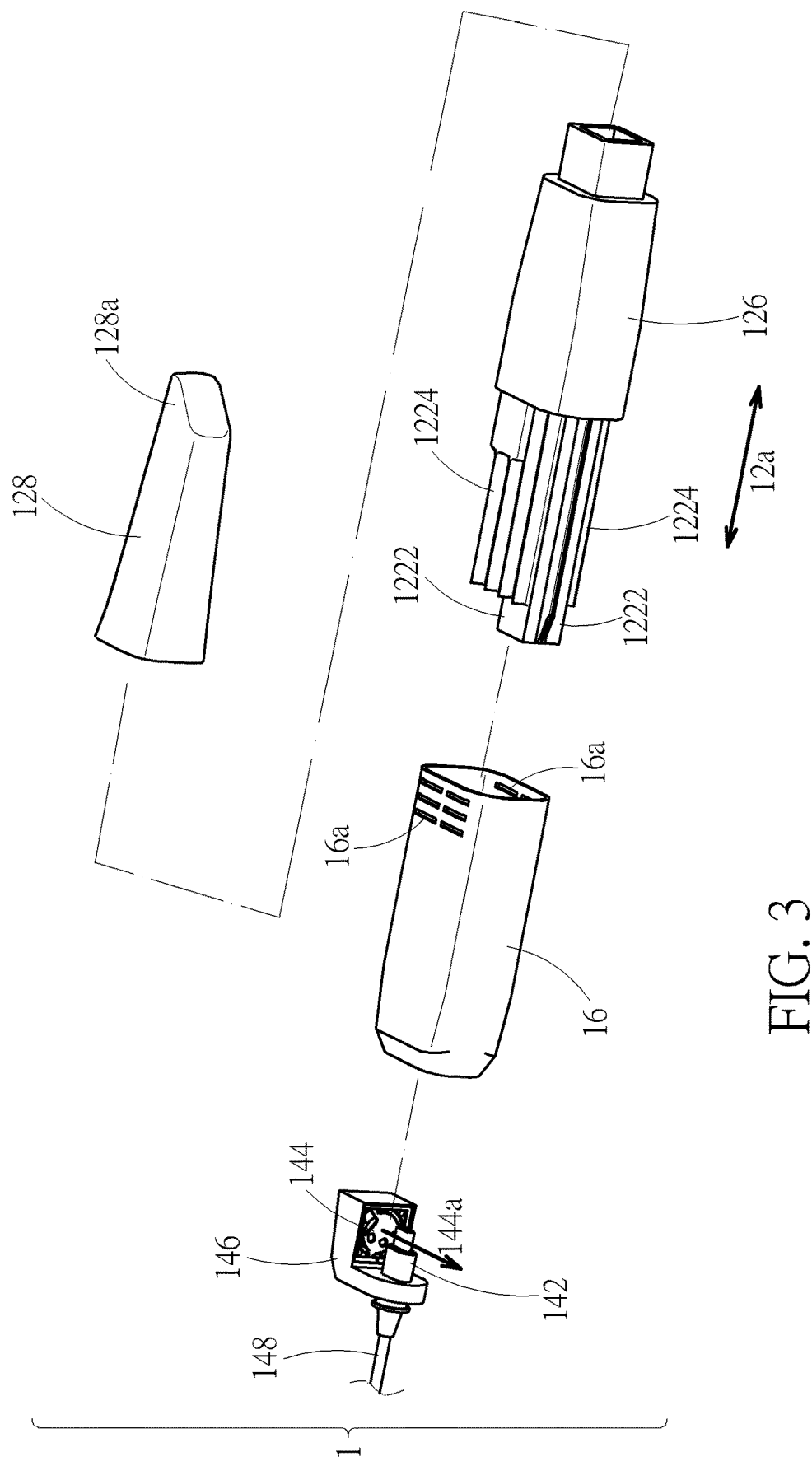
FIG. 3 is a schematic diagram illustrating the intraoral scanner in FIG. 2 in another view point.
Figure 4:
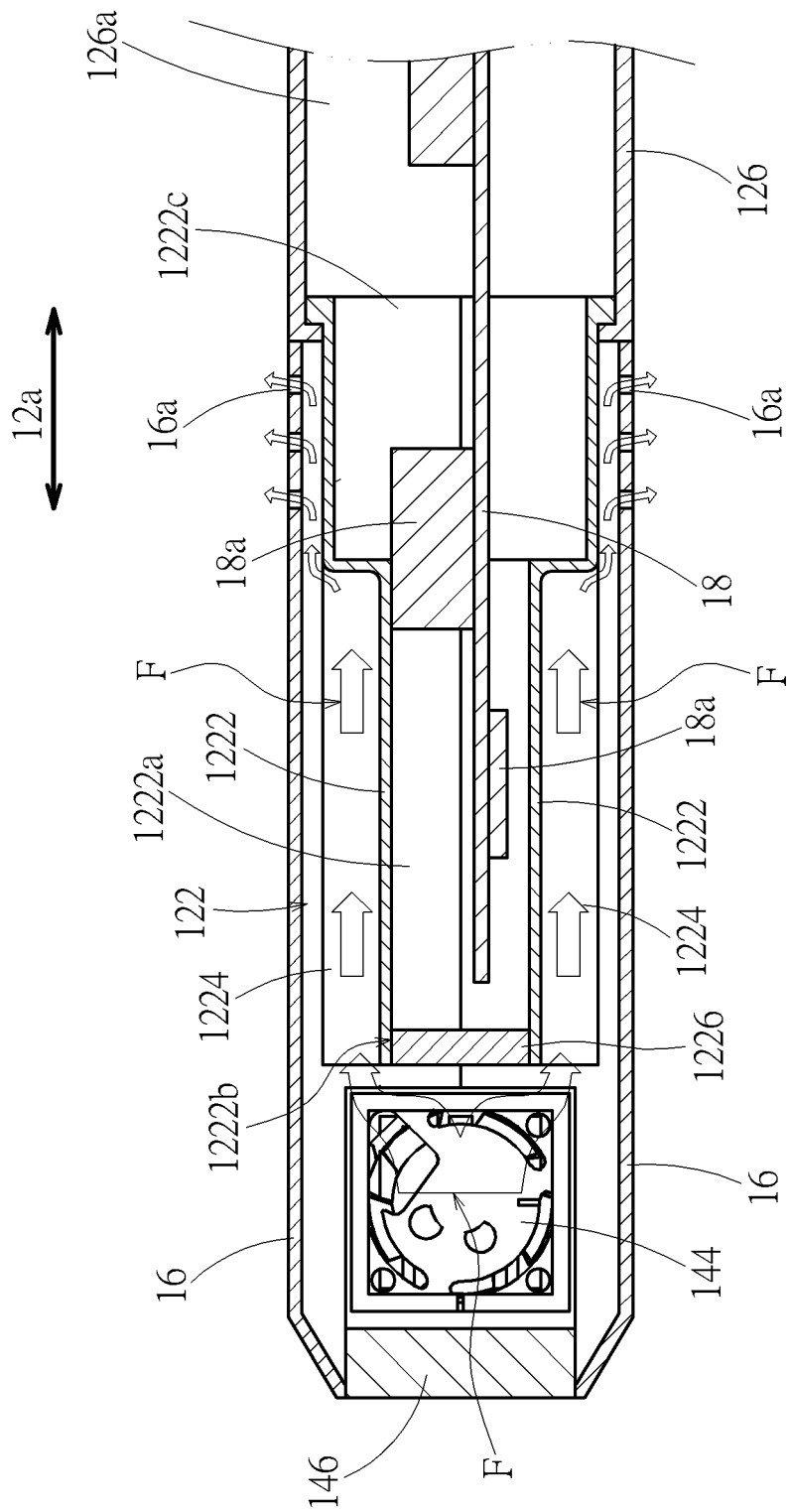
FIG. 4 is a sectional view of a portion of the intraoral scanner along the line X-X in FIG. 1.

Please refer to FIG. 1 to FIG. 4. An intraoral scanner 1 according to an embodiment includes a device body 12, a connection portion 14, and a guiding cover 16. The device body 12 has a heat-dissipating structure 122 and a first electrical connection port 124. The main components of the intraoral scanner 1 are disposed inside the device body 12. Heat generated by the main components during operation will dissipate through the heat-dissipating structure 122. The connection portion 14 is detachably connected to the device body 12 and includes a second electrical connection port 142 and a fan 144. The second electrical connection port 142 and the first electrical connection port 124 are connected, so that the device body 12 can be powered through the connection portion 14 and can communicate with external devices (e.g. computer hosts). The fan 144 (e.g. but not limited to an axial fan) generates an airflow F (of which the following path is indicated by hollow arrows in FIG. 1 and FIG. 4) that flows through the heat-dissipating structure 122 for enhancing the heat-dissipating efficiency of the heat-dissipating structure 122. The guiding cover 16 is connected to the connection portion 14 and the device body 12 and covers the heat-dissipating structure 122 so that the airflow F flows between the guiding cover 16 and the heat-dissipating structure 122, which enhances the heat-dissipating efficiency of the heat-dissipating structure 122 further. By detaching the device body 12 from the connection portion 14 (and the guiding cover 16), the device body 12 can be cleaned and sterilized individually without being affected by the fan 144 and other moving parts.

Figure 5:
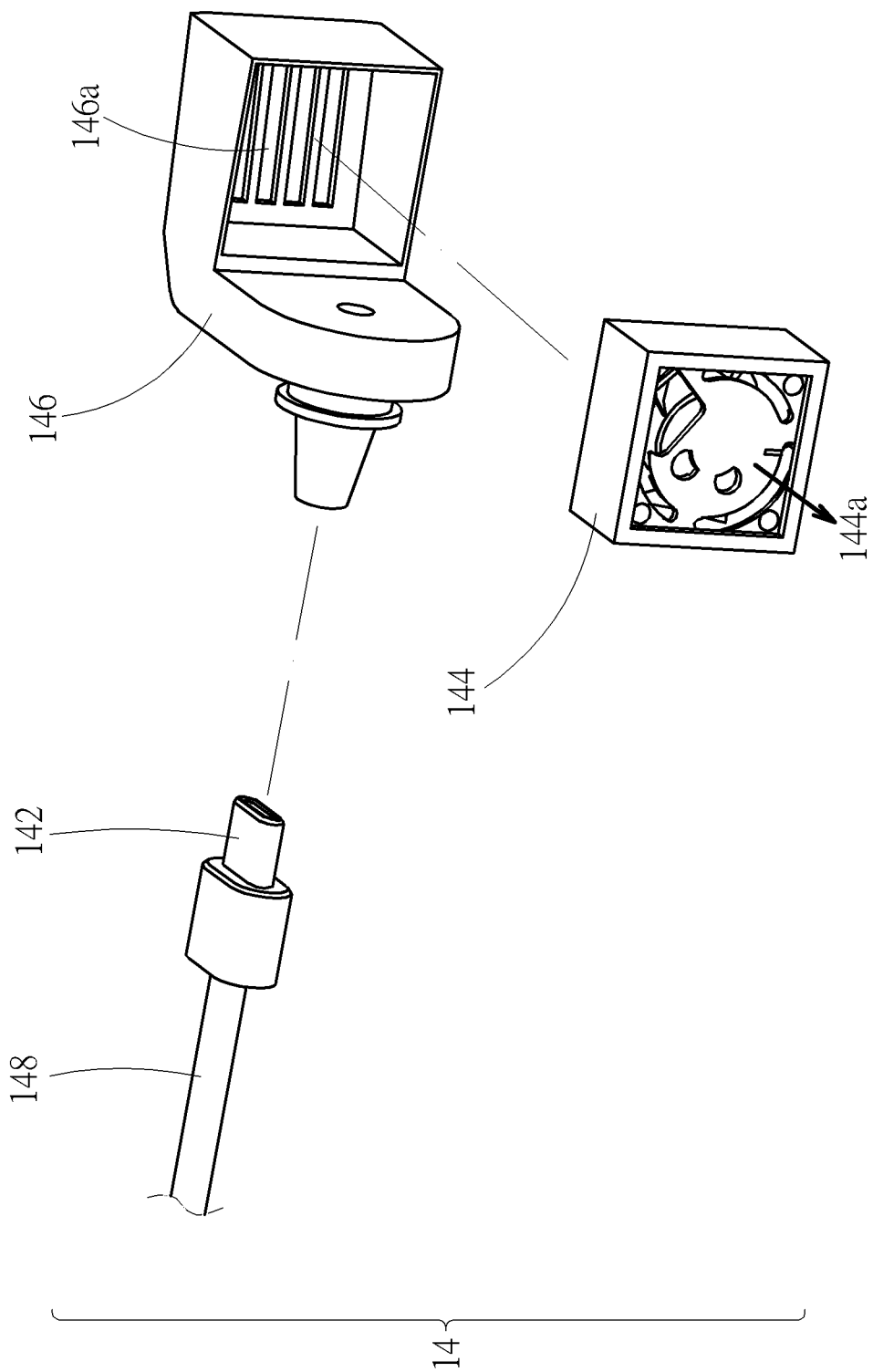
FIG. 5 is an exploded view of a connection portion of the intraoral scanner in FIG. 2 in another view point.
Figure 6:
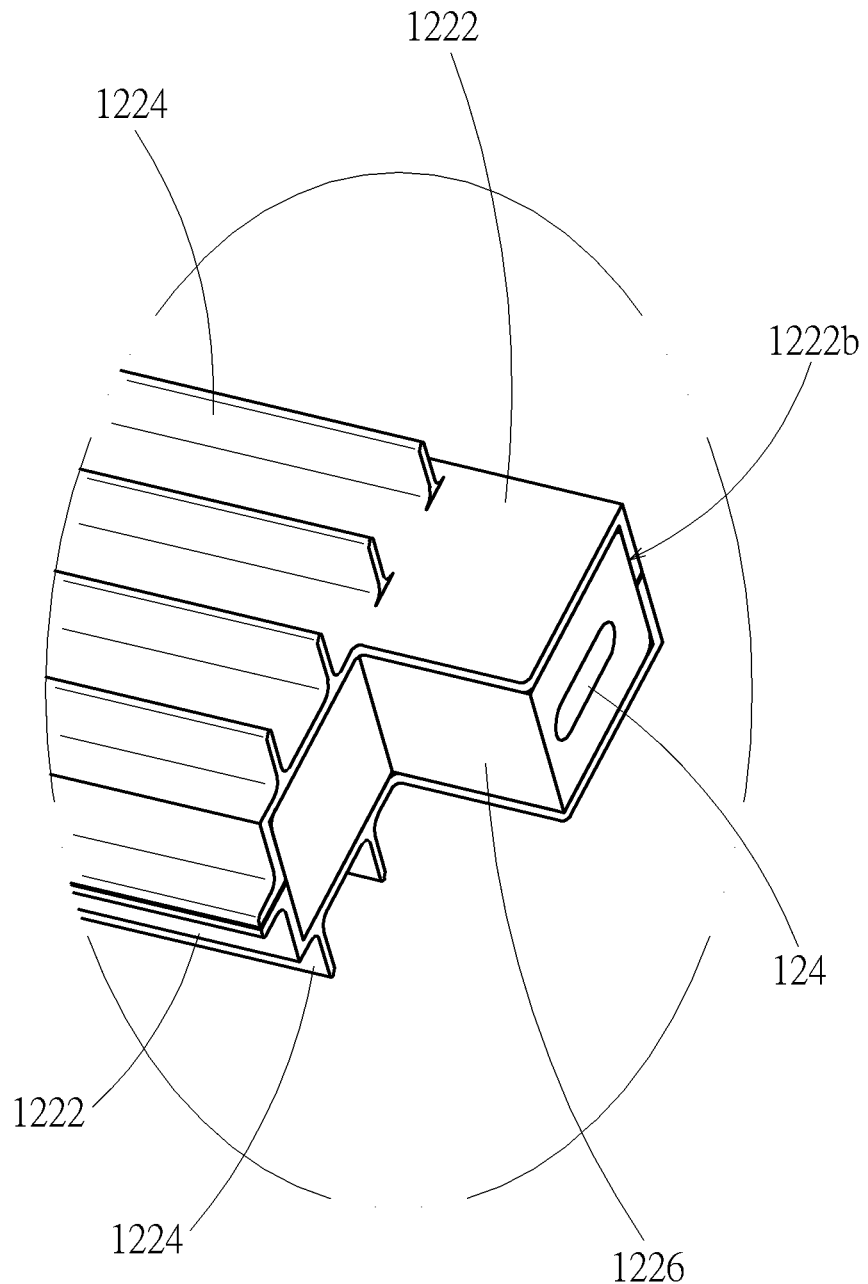
FIG. 6 is an enlarged view of the circle A in FIG. 2.
Figure 7:
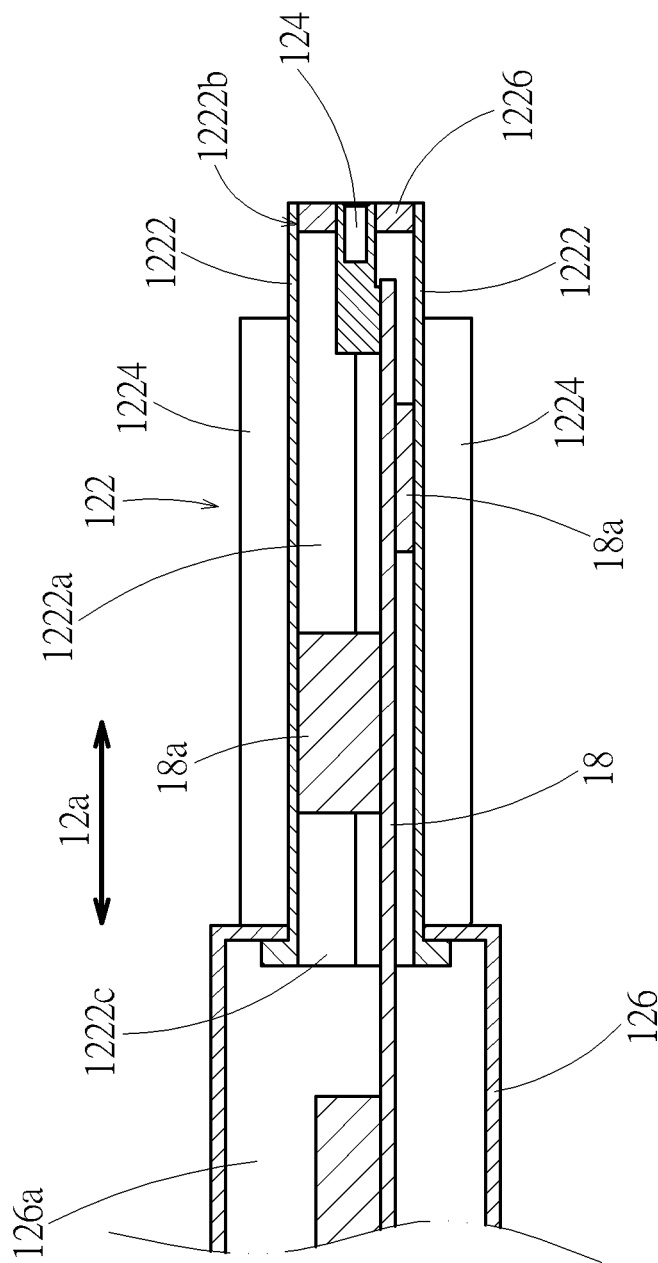
FIG. 7 is a sectional view of a heat-dissipating structure in FIG. 2 along the line Y-Y.

Please refer to FIG. 5 to FIG. 7. The device body 12 as a whole shows a long bar and has a longitudinal axis direction 12a. The device body 12 includes a main portion 126 and a probe portion 128. The probe portion 128 and the heat-dissipating structure 122 are located at two opposite sides of the device body 12 relative to the longitudinal axis direction 12a. Therein, the probe portion 128 is detachably connected to the main portion 126. The heat-dissipating structure 122 is fixed to the main portion 126. The main portion 126 is located between the probe portion 128 and the heat-dissipating structure 122 in the longitudinal axis direction 12a. The heat-dissipating structure 122 is located between the probe portion 128 and the connection portion 14 in the longitudinal axis direction 12a. When using the intraoral scanner 1, a user can hold the main portion 126 by hand to put the probe portion 128 into an oral cavity and then implements scanning through a tip 128a of the probe portion 128. By detaching the probe portion 128, the probe portion 128 and the main portion 126 (together with the heat-dissipating structure 122) can be cleaned and sterilized individually. In practice, the main portion 126 and the heat-dissipating structure 122 can be designed to be structurally integrated as a whole to be waterproof, which facilitates soaking and is also conducive to flushing, scrubbing, and soaking for sterilization. Furthermore, in another embodiment, the probe portion 128 and the main portion 126 are fixedly connected, and the device body 12 as a whole is designed to be waterproof, which is conducive to flushing, scrubbing, and soaking for sterilization of the device body 12.

In the embodiment, the heat-dissipating structure 122 includes a heat-conductive casing 1222, a plurality of fins 1224, and a cover 1226. The fins 1224 extends outward from the heat-conductive casing 1222. The heat-conductive casing 1222 has an inner accommodating space 1222a and openings 1222b and 1222c communicating with the inner accommodating space 1222a. The cover 1226 is fixed to the heat-conductive casing 1222 to cover the cover opening 1222b. The first electrical connection port 124 is disposed on the cover 1226. The heat-conductive casing 1222 fits tightly with the main portion 126 through the opening 1222c. The inner accommodating space 1222a of the heat-conductive casing 1222 and an inner accommodating space 126a of the main portion 126 together accommodate the circuit board 18. Heat-generating components 18a (e.g. but not limited to processing chips, power transistors, LED light sources and so on) on the circuit board 18 can be thermally coupled to an inner wall surface of the heat-conductive casing 1222 (e.g. by direct contact or through compound). In the embodiment, the heat-conductive casing 1222 is formed by two casings connected with each other, but can alternatively be formed by a single structure in practice. Furthermore, the cover 1226 fits tightly with the opening 1222b. The first electrical connection port 124 (e.g. waterproof USB Type-C connector, of which the waterproof rating can be IPX4 to IPX8; in FIG. 7, which is shown by a single block for drawing simplification) fits tightly with the cover 1226, so that the device body 12 as a whole is waterproof.

In the embodiment, the connection portion 14 includes a fixing base 146 and a cable 148. The second electrical connection port 142 (e.g. USB Type-C connector, mated with the first electrical connection port 124) and the fan 144 are fixed on the fixing base 146. The cable 148 is electrically connected to the second electrical connection port 142 and the fan 144 and extends out the fixing base 146. Through the cable 148, the intraoral scanner 1 can be powered from the outside and can communicate with external devices (e.g. computer hosts). It is noted that, in other embodiments, the fan 144 is not limited to be directly electrically connected to the cable 148, and it is practicable to electrically connect the fan 148 with an independent connection port on the cover 1226 through spring clips or elastic terminal (pogo pin). The fixing base 146 has a vent 146a corresponding to the fan 144. The airflow F generated by the fan 144 passes through the vent 146a and flows through the fins 1224. The guiding cover 16 is connected to the fixing base 146 and covers the fins 1224. The airflow F flows between the guiding cover 16, the heat-conductive casing 1222, and the fins 1224. The guiding cover 16 has at least one vent 16a. The fins 1224 are located between the fan 144 and the vent 16a. This structural configuration can ensure that the airflow F can effectively flow through the fins 1224. Furthermore, the guiding cover 16 also has the function of isolating the heat-dissipating structure 122, so that when operating the intraoral scanner 1, the user can avoid directly contacting the hot heat-dissipating structure 122.

Furthermore, in the embodiment, the fins 1224 are disposed at both top and bottom sides of the heat-dissipating structure 122. The guiding cover 16 also forms the vent 16a corresponding to the fins 1224 on the top and bottom sides of the heat-dissipating structure 122 respectively. The fan 144 draws in external air through the vent 146a to form the airflow F. The airflow F will split to flow through the upper and lower fins 1224 and then flow out the guiding cover 16 through the corresponding vent 16a. In practice, it is practicable to form an airflow (of which the flowing direction is opposite to that of the above airflow F) by using the fan 144 to extract air out through the vent 146a. This airflow combines airflows from the upper and lower fins 1224 (which are formed by drawing in external air through the corresponding vent 16a). The above both airflow configurations can effectively enhance the heat-dissipating efficiency of the heat-dissipating structure 122.

Furthermore, in the embodiment, the structural connection of the first electrical connection port 124 and the second electrical connection port 142 is also conducive to the strength of the connection of the connection portion 14 and the device body 12. In practice, it is practicable to structurally connect the fixing base 146 of the connection portion 14 with the heat-dissipating structure 122, which can enhance the strength of the connection of the connection portion 14 and the device body 12. In addition, in the embodiment, the guiding cover 16 is realized by a single part (e.g. in a form of barrel); however, in practice, the guiding cover 16 can be realized by a combined component.

In addition, in the embodiment, the first electrical connection port 124 and the second electrical connection port 142 are realized by connectors. However, in practice, the first electrical connection port 124 and the second electrical connection port 142 can be realized by metal spring clips and conductive pads that can contact each other for electrical connection. For example, the first electrical connection port 124 includes a plurality of conductive pads (e.g. structurally integrated into the cover 1226 by insert molding). The second electrical connection port 142 includes a plurality of corresponding metal spring clips (e.g. fixed on the fixing base 146 and electrically connected to the cable 148). The fixing base 146 of the connection portion 14 can be structurally connected to the device body 12 (e.g. the heat-dissipating structure 122 thereof) through the guiding cover 16 or through other structure of the fixing base 146 (e.g. the fixing base 146 and the heat-dissipating structure 122 are structurally engaged by hooks/slots or holes/posts), so that the metal spring clips abut against the corresponding conductive pads leading to the electrical connection of the first electrical connection port 124 and the second electrical connection port 142.

Figure 8:
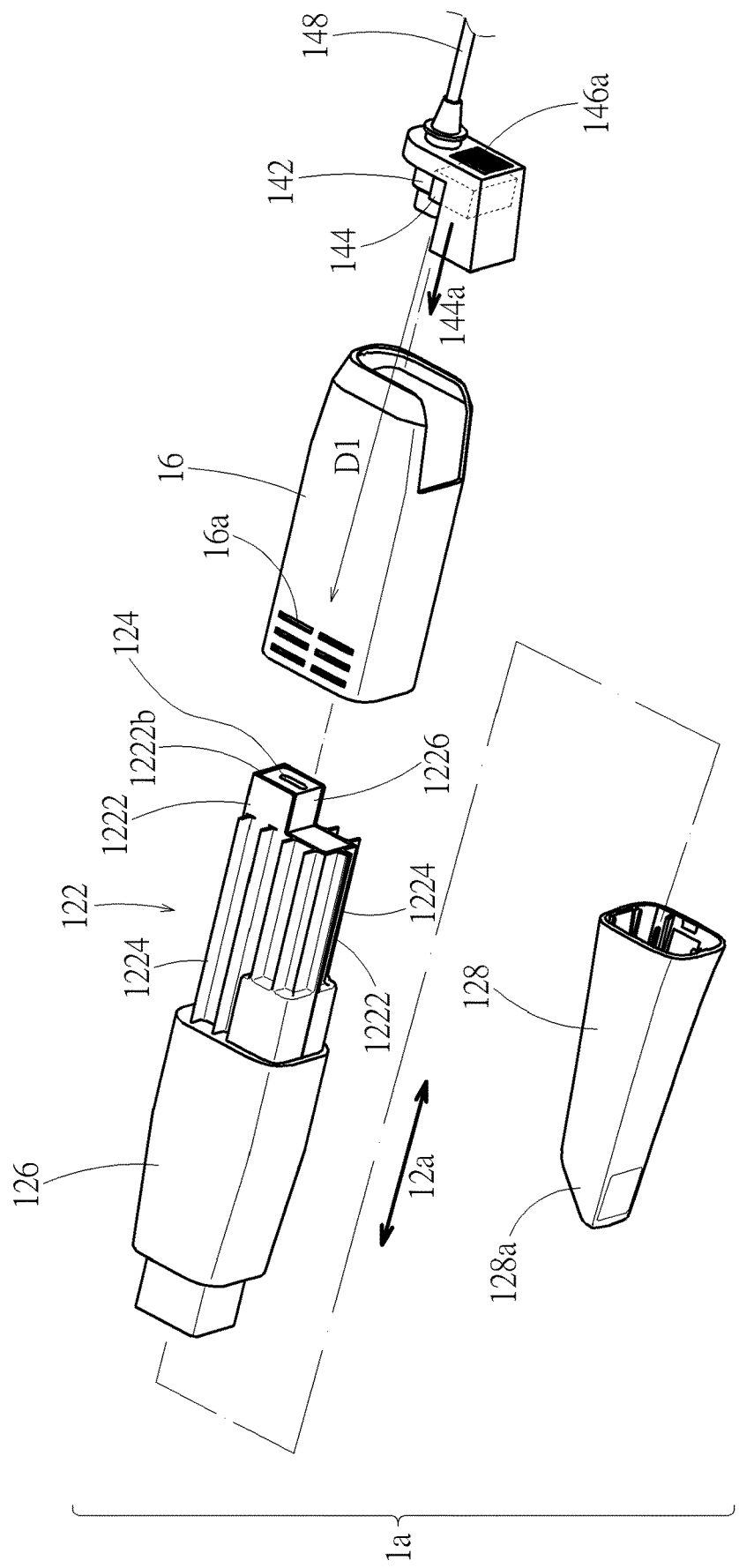
FIG. 8 is a partially exploded view of an intraoral scanner according to another embodiment.

Furthermore, in the embodiment, the fins 1224 is substantially extend parallel to the longitudinal axis direction 12a. Although a direction 144a of the fan 144 (i.e. the direction in which the airflow is formed) is almost perpendicular to the extension direction of the fins 1224, it is practicable in principle to make the direction 144a of the fan 144 substantially parallel to the extension direction of the fins 1224 by changing the disposition of the fan 144 so that the resistance to the airflow F can be reduced. As shown by FIG. 8, in an intraoral scanner 1a according to another embodiment, the fan 144 thereof (of which the portion covered by the fixing base 146 is shown in hidden lines in FIG. 8) is disposed at an end of the fixing base 146 in the longitudinal axis direction 12a. A direction D1 is defined as pointing from the fan 144 to the vent 16a. The direction 144a of the fan 144 is parallel to the direction D1. The fins 1224 extend substantially parallel to the direction D1.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An intraoral scanner, comprising:
   a device body, having a probe portion, a heat-dissipating structure and a first electrical connection port, the device body having a longitudinal axis direction, the probe portion and the heat-dissipating structure being located at two opposite sides of the device body relative to the longitudinal axis direction; and
   a connection portion, detachably connected to the device body, the heat-dissipating structure being located between the probe portion and the connection portion, the connection portion comprising a second electrical connection port and a fan, the second electrical connection port and the first electrical connection port being connected, the fan generating an airflow flowing through the heat-dissipating structure.

2. The intraoral scanner according to claim 1, wherein the heat-dissipating structure comprises a heat-conductive casing and a plurality of fins extending outward from the heat-conductive casing, and the airflow flows through the fins.

3. The intraoral scanner according to claim 2, further comprising a guiding cover that is connected to the connection portion and the device body and covers the fins, wherein the airflow flows between the guiding cover, the heat-conductive casing, and the fins.

4. The intraoral scanner according to claim 3, wherein the guiding cover has a vent, and the fins are located between the fan and the vent.

5. The intraoral scanner according to claim 4, wherein a direction is defined as pointing from the fan to the vent, and the fins extend parallel to the direction.

6. The intraoral scanner according to claim 1, wherein the device body is waterproof.

7. The intraoral scanner according to claim 1, wherein the device body comprises a main portion, the probe portion is detachably connected to the main portion, the heat-dissipating structure is fixed to the main portion, and the probe portion and the heat-dissipating structure are located on two opposite sides of the main portion.

8. The intraoral scanner according to claim 7, wherein the main portion and the heat-dissipating structure as a whole are waterproof.

9. The intraoral scanner according to claim 1, wherein the heat-dissipating structure comprises a heat-conductive casing, a plurality of fins, and a cover, the fins extend outward from the heat-conductive casing, the heat-conductive casing has an inner accommodating space and an opening communicating with the inner accommodating space, the cover is fixed to the heat-conductive casing to cover the opening, and the first electrical connection port is disposed on the cover.

10. The intraoral scanner according to claim 1, wherein the connection portion comprises a fixing base and a cable, the second electrical connection port and the fan are fixed on the fixing base, and the cable is electrically connected to the second electrical connection port and the fan and extends out from the fixing base.

* * * * *